United States Patent [19]

Wechter et al.

[11] Patent Number: 4,501,754

[45] Date of Patent: Feb. 26, 1985

[54] METHODS OF TREATING BONE RESORPTION

[75] Inventors: William J. Wechter, Kalamazoo, Mich.; John E. Horton, Framingham, Mass.

[73] Assignee: The Upjohn Company, Kalamazoo, Mich.

[21] Appl. No.: 360,020

[22] Filed: Mar. 19, 1982

Related U.S. Application Data

[63] Continuation of Ser. No. 168,827, Jul. 10, 1980, abandoned, which is a continuation-in-part of Ser. No. 73,398, Sep. 7, 1979, abandoned, and Ser. No. 73,400, Sep. 7, 1979, abandoned.

[51] Int. Cl.$^3$ .................... A61K 31/35; A61K 31/275
[52] U.S. Cl. ..................................... 514/456; 514/616
[58] Field of Search .................. 424/49, 2, 309, 304, 424/283

[56] References Cited

U.S. PATENT DOCUMENTS 4,089,973  5/1978  Hall et al. .......................... 424/304

*Primary Examiner*—Albert T. Meyers
*Assistant Examiner*—John W. Rollins
*Attorney, Agent, or Firm*—L. Ruth Hattan

[57] ABSTRACT

The present invention provides novel methods and compositions for treatment of pathological mineral resorptive states (PAMIRS), e.g., osteoporosis, employing disodiumchromoglycate (DSCG) and antiallergenic biologues, including other bis chromones, benzopyrans, and oxamates.

2 Claims, No Drawings

METHODS OF TREATING BONE RESORPTION

The research described herein was supported in part by grants from the National Institutes of Health (SO7 RR 05318).

DESCRIPTION

Process and Composition

CROSS REFERENCE TO RELATED APPLICATIONS

This application is a continuation of application Ser. No. 168,827 filed July 10, 1980, now abandoned, which is a continuation-in-part of U.S. Ser. Nos. 073,398 and 073,400 filed Sept. 7, 1979, now abandoned.

BACKGROUND OF THE INVENTION

The present invention relates to novel methods of using known pharmacological agents. The invention further relates to novel compositions employing these known pharmacological agents for the treatment of various conditions or diseases in animals. Particularly, the present invention relates to the use of these known pharmacological agents in the treatment of pathological mineral resorptive states in animals.

The mineral resorptive states whose treatment comprises the subject matter of the present invention are those states arising from physiological processes, particularly frankly pathological processes, in which loss of skeletal or dental structure transpires.

The mineral resorptive states characterized by the loss of dental structure include, for example, surface and/or inflammatory resorption of the dental root structure and dental ankylosis with replacement resorption. The dental demineralization resultant from these states is well known and they are readily diagnosed by an attending dentist or veterinarian.

The mineral resorptive states directly involving loss of skeletal structure include a wide variety of diseases and conditions. Further, certain mineral resorptive states are a recognized untoward consequence of numerous other diseases and conditions.

One principal class of mineral resorptive states are the various forms or types of osteoporosis. Osteoporosis refers to the abnormal rarefaction of bone, due to the failure of osteoblast to lay down bone matrix, excessive osteoclastic activity, or other disturbances of the osteoblastic-osteoclastic equilibrium. Rarefaction of bone refers to the condition of its becoming or being less dense, that is, being reduced in density, but not in volume. Osteoblasts are the cells which carry out the function of producing bone, and they function in the healthy vertebrate together with osteoclasts, cells whose function it is to absorb and remove bone.

Osteoporosis is a condition common in adults and typically results in a decrease in density of both the bone matrix (the substrate, collagen), and the bone mineral, $Ca^{10}(PO^4)^6(OH)^2$ or "hydroxyapatite". Osteoporosis typically results in numerous symptomatic manifestations, including back pain and deformation of the back bone. The bones of the afflicted animal also become brittle, which increases the likelihood and incidences of fractures. Various types of osteoporosis are known. See for example Dorland's Illustrated Medical Dictionary, 24th Edition, W. B. Saunders Company, London (1965). Among the types of osteoporosis are senile, attributed to the aging process; post-menopausal, attributable to the decreased ovarian production of estrogen following memopause; disuse, as a result of longterm immobilization; and steroidal, consequent to treatment with antiinflammatory steroids. Other notable disease states whose principal long-term pathology arises from a mineral resorptive state as a constituent thereof include Paget's disease, rheumatoid arthritis, and periodontal disease. For example, Paget's disease is characterized by initial bone decalcification and softening, followed by an abnormal calcium deposition. The abnormal recalcification leads to deformed bones and other untoward consequences. Somewhat similar in its ultimate effect is the pathological mineral resorptive state resulting from rheumatoid arthritis. In this disease condition, the inflammation of synovial tissues results in the demineralization of contiguous bone surfaces and abnormal mineralization of noncontiguous surfaces. The long-term effect of this disease process is typically immobilization of the affected joints due to the progressive malformation of bone structure. Finally, periodontal disease is also characterized by a pathological mineral resorptive state, which results in the resorption of the alveolar bone. The alveolar bone functions to support and anchor the teeth and its progressive resorption results in the loosening and subsequent loss of affected teeth.

Other disease conditions also induce mineral resorptive states in skeletal structures with resulting untoward effects on the affected animal. For example, hyperparathyroidism results in the excessive production of PTH (parathyroid hormone), an agent known to stimulate osteoclastic activity. Further, in many neoplastic diseases, the neoplasms, on contact with skeletal structures, induce pathological mineral resorptive states with resulting pathological consequences. For example, numerous types of mammary carcinoma cells are known to induce this pathological state.

Other neoplastic diseases also have the effect of inducing a pathological mineral resorptive state in skeletal structures. Such diseases include plasmacytomas, e.g., multiple myloma. For example, the latter disease is known to induce the production of excessive amounts of OAF (osteoclast activating factor), which results in excessive osteoclastic activity and consequent resorption of skeletal structures.

Finally, while the mineral resorptive state generally has attributed in the past to the excess activity of osteoclasts, to disturbances in the osteoblastic-osteoclastic equillibrium, and/or to infiltration of mineral tissues by neoplastic cells, the mineral resorptive state also may arise from activities of other cell types, solely, or in combination (for reference see Mindy, G.R., et al., "Direct Resorption of Bone by Human Monocytes", Science 196:1109–1111, 1977; Heersche, J. N. M., "The Mechanism of Osteoclastic Bone Resorption: A New Hypothesis", Proceedings, Mechanism of Localized Bone Loss, Eds., Horton, Tarpley, and Davis, Special Supplement to Calcified Tissue Abstracts, pp. 437–438, 1978; and Teitelbaum, S.L., et al., "Contact-Mediated Bone Resorption by Human Monocytes in Vitro", Proceedings, Mechanism of Localized Bone Loss, Eds., Horton, Tarpley, and Davis, Special Supplement to Calcified Tissue Abstracts, p. 443, 1978). Therefore, a mineral resorptive state may arise from a variety of cell-mediated events to result in the loss of skeletal or dental tissue.

Numerous antiosteoporotic agents, i.e., agents proposed for the treatment or prevention of osteoporosis, are known in the art. Such agents include anabolic steroids, various phosphorus-containing agents, vitamin D and related substances, estrogenic steroids, and calcitonin. Also, certain aromatic carboxylic acids have been described as useful antiosteoporotic agents. For a detailed review and discussion of such antiosteoporotic agents, see U.S. Pat. Nos. 4,125,621 or 4,101,688.

Numerous methods have been reported for assessing the effectiveness of antiosteoporotic agents. For example, one such report indicates that the effectiveness of any given antiosteoporotic agent may be determined by measuring the effect of such an agent on the production of cyclic AMP, utilizing isolated bone cells as the test medium according to the methods of Rodan, et al., J. B. C. 429:306 (1974) and Rodan, et al., Science 189:467 (1975). See U.S. Pat. No. 4,125,621 (Example 1) for a detailed description of this procedure.

An efficient means of assessing the inhibition of mineral resorptive states by a chemical agent is described by Horton, J. E., et al., "Inhibition of the In Vitro Bone Resorption by a Cartilage-Derived Anticollagenase Factor", Science 199:1342–1345 (Mar. 24, 1978). The method of Horton, et al. determines the ability of a chemical agent to block OAF, prostaglandin, and parathyroid hormone-stimulated (PTH-stimulated) $^{45}Ca$ release from fetal rat bone in vitro. The relationship between the activity of osteoclasts in bone resorption and the acceleration of bone resorptive states induced by PTH-stimulation, both in vivo and in vitro is known. See Rasmussen, H., et al., "The Physiologic and Cellular Basis of Metabolic Bone Disease", Williams & Williams, Baltimore, 1974, pages 144–154.

The technique of Horton for measuring the inhibition of mineral resorptive states employs bone culture techniques described by Raisz, L. G., et al., Endocrinology 85:446 (1969). Paired shafts of the radius and ulna from 19 day old rat fetuses are radioactively labelled by injection of the mother with $^{45}Ca$ on the day prior to culturing. The shafts are then cultured in the described medium containing (optionally) the chemical agent to be tested and/or a bone resorption stimulating agent such as PTH.

Mineral resorption of the skeletal structure is stimulated by addition of PTH/ml, typically 2.5 IU (International Units) every 48 hours. Cultures are maintained for 120–144 hours and the medium changed every 48 hours. The percentage of $^{45}Ca$ released from bone into the culture medium is then used as a measure of bone resorption. The degree of mineral resorption is determined by liquid scintillation spectrometry from the counts per minute of $^{45}Ca$ radioactivity present in the culture medium.

The known compounds employed in the novel methods and compositions disclosed herein are anti-allergenic agents, specifically including disodiumchromoglycate (DSCG) and DSCG anti-allergenic biologues. DSCG anti-allergenic biologues include anti-allergenic bis chromones related to DSCG as are described in U.S. Pat. No. 3,419,578. Further related anti-allergenic bis chromones are those described in U.S. Pat. Nos. 3,519,652 and 3,673,218. Moreover, DSCG anti-allergenic biologues, including anti-allergenic uses therefor, are described in U.S. Pat. No. 4,046,910, issued Sept. 6, 1977. The description of DSCG and related anti-allergenic bis chromones and their anti-allergenic compositions are incorporated here by reference from U.S. Pat. Nos. 3,419,578 and 4,046,910.

Another class of DSCG anti-allergenic biologues are the anti-allergenic benzopyrans, particularly the compounds described in U.S. Pat. Nos. 4,159,273, 3,786,071, 3,952,104, and 4,055,654. Notable among these compounds is proxicromil (FPL 57,787), 6,7,8,9-tetrahydro-5'-hydroxy-4-oxo-10-propyl-4H-naphtho[2,3-6]pyran-2-carboxylic acid, described in Example 8 of U.S. Pat. No. 4,159,273. The description and anti-allergenic compositions of these anti-allergenic benzopyrans is incorporated here by reference from U.S. Pat. Nos. 4,159,273, 3,786,071, 4,055,654, and 3,952,104.

Yet another class of DSCG anti-allergenic biologues are the anti-allergenic oxamic acids or derivatives thereof. These compounds, together with their anti-allergenic uses and compositions, are described in U.S. Pat. Nos. 3,993,679, 4,159,278, 4,095,028, 4,089,973, 4,011,337, 4,091,011, 3,972,911, 4,067,995, 3,980,660, 4,044,148, 3,982,006, 4,061,791, 4,017,538, 4,119,783, 4,113,880, 4,128,660, 4,150,140, 3,966,965, 3,963,660, 4,038,398, 3,987,192, 3,852,324, 3,836,541, and 3,836,164. The preparations of such compounds and their anti-allergenic compositions are incorporated by reference here from the aforementioned United States patents. One important anti-allergenic oxamate is iodoxamide, N,N'-(2-chloro-5-cyano-m-phenylene)amino methane salt.

PRIOR ART

DSCG and its anti-allergenic biologues and anti-allergenic uses therefor are known in the art. See the various U.S. patents cited above. Further known are numerous anti-osteoporotic agents. See U.S. Pat. Nos. 4,121,621 and 4,101,688 for a summary of such agents.

With respect to DSCG, this agent has been reported to show no detectable effect on gingivitis in the monkey, although DSCG was reported to inhibit mast cell degranulation of monkey gingiva. See Nuki, K., et al., "The Inhibition of Mast Cell Degranulation in Monkey Gingiva by Disodium Cromoglycate", J. Periodontal. Res. 10:282–287 (1975) and references cited therein. Two references of particular interest cited therein are Goldhaber, P., "Heparin Enhancement of Factors Stimulating Bone Resorption in Tissue Culture", Science 147:407–408 (1965), and Shapiro, S., et al., "Mass Cell Population in Gingiva Affected by Chronic Destructive Periodontal Disease", Periodontics 40:276–278 (1969).

SUMMARY OF THE INVENTION

The present invention particularly provides:

(1) A method of arresting or preventing a pathological mineral resorptive state (PAMIRS) in an animal exhibiting or susceptible to development of said PAMIRS which comprises:

systemically administering to said animal an amount of an anti-PAMIRS DSCG biologue effective to treat or prevent said PAMIRS;

(2) In a method of preventing or treating a pathological mineral resorptive state (PAMIRS) with one or more known antiosteoporotic agents selected from the group consisting of anabolic steriods, estrogenic steroids, vitamin D and its metabolites, phosphorous-containing agents, inorganic fluoride-containing agents, calcium salts, and calcitonin, the improvement which comprises:

concomitantly administering an amount of an anti-PAMIRS DSCG biologue which, together with said known antiosteoporotic agent or agents, is effective to prevent or arrest said PAMIRS;

(3) In a method of treating an inflammatory disease with an anti-inflammatory steroid, the improvement which comprises:

concomitantly administering an amount of an anti-pathological mineral resorptive state (anti-PAMIRS) DSCG biologue effective to prevent or arrest a pathological mineral resorptive state (PAMIRS) resulting from said anti-inflammatory steroid;

(4) In a unit does of a pharmaceutical composition for preventing or treating a pathological mineral resorptive state (PAMIRS) with one or more known anti-osteoporotic agents selected from the group consisting of anabolic steroids, estrogenic steroids, vitamin D and its metabolites, phosphorus-containing agents, inorganic fluoride-containing agents, calcium salts, and calcitonin, the improvement which comprises:

an amount of an anti-PAMIRS DSCG biologue which, together with said known anti-osteoporotic agent or agents, is an effective unit dose to prevent or arrest said PAMIRS;

(5) In a unit dose of a pharmaceutical composition for treating inflammatory diseases with an anti-inflammatory steroid, the improvement which comprises:

an amount of an anti-pathological mineral resorptive state (anti-PAMIRS) DSCG biologue which is an effective unit dose to prevent or arrest a pathological mineral resorptive state (PAMIRS) resulting from said administration of said anti-inflammatory steroid;

(6) A dentifrice for administration to a mammal suffering from or susceptible to the development of a dental pathological mineral resorptive state (PAMIRS) or periodontal disease which comprises:

an anti-PAMIRS DSCG biologue present therein in a concentration such that a pre-determined volume thereof contains an amount of said anti-PAMIRS DSCG biologue effective to arrest or prevent said dental PAMIRS or arrest or prevent a PAMIRS secondary to said periodontal disease when applied to the oral tissues of said mammal in a conventional manner;

(7) A mouthwash for administration to a mammal suffering from or susceptible to the development of a dental pathological mineral resorptive state (PAMIRS) or periodontal disease which comprises:

an anti-PAMIRS DSCG biologue present therein in a concentration such that a pre-determined volume thereof contains an amount of said anti-PAMIRS DSCG biologue effective to arrest or prevent said dental PAMIRS or arrest or prevent a PAMIRS secondary to said periodontal disease when applied to the oral tissues of said mammal in a conventional manner;

(8) An animal feed for feeding to an animal suffering from or susceptible to the development of a pathological mineral resorptive state (PAMIRS) which comprises:

an anti-PAMIRS DSCG biologue in a concentration such that an amount thereof which will be ingested by the animal over a pre-determined interval contains an amount of said anti-PAMIRS DSCG biologue effective to arrest or prevent said PAMIRS during said pre-determined interval; and (9) A feed premix for preparing an animal feed for feeding to an animal suffering from or susceptible to the development of a pathological mineral resorptive state (PAMIRS) which comprises:

an anti-PAMIRS DSCG biologue in a concentration such that, when said animal feed premix is diluted with animal feed in a pre-determined ratio, an amount of said anti-PAMIRS DSCG biologue in said animal feed which will be ingested by the animal over a pre-determined interval contains an amount of said anti-PAMIRS DSCG biologue during said pre-determined interval effective to arrest or prevent said PAMIRS.

The present invention relates to the treatment of animals, although mammals and domesticated fowl represent particularly preferred embodiments of the present invention. Most preferred is the treatment of humans by the instant method. The present invention thus provides a method of treating both humans and valuable domestic mammals, such as bovine, equine, canine, and feline species, and chickens, turkeys, geese, ducks, and other fowl.

The present invention relates to the arrest or prophylaxis of pathological mineral resorptive state or "PAMIRS". The employment of sound medical therapy requires that the anti-PAMIRS agent be employed prophylactically only in cases where the animal or patient is particularly susceptible to the development of a PAMIRS. The conditions and circumstances which increase susceptibility are readily ascertainable to the ordinarily skilled dentist, physician or veterinarian and include:

(1) long term, high dose therapy with an anti-inflammatory steroid;
(2) ovario-hysterectomy;
(3) menopause;
(4) old age;
(5) interceptive, repairative, and/or corrective surgical procedures involving diseased, deformed, and/or transplanted mineralized tissue;
(6) space travel for prolonged periods under reduced gravitational forces;
(7) renal dialysis; and
(8) a diagnosis of any disease or condition in which a PAMIRS is a potential consequence, e.g., periodontal disease.

In the prophylactic use of these anti-PAMIRS agents, the dose effective for the prevention of the PAMIRS is determined by patient or animal response, as discussed hereinafter for therapeutic uses, and is, in general, somewhat less than the dose required to treat a PAMIRS.

A PAMIRS which is arrested or prevented in accordance with the present invention includes each of the various states or conditions described above where the long-term effects on the animal are untoward, and hence the condition or state is associated with a direct or indirect pathological process.

A PAMIRS is not an uncommon condition encountered in dental, medical, or veterinary practice. Accordingly, the diagnosis of a PAMIRS is readily undertaken by the ordinarily skilled dentist, physician or veterinarian.

The dosage regimen for the anti-PAMIRS DSCG biologue employed is selected in accordance with a variety of factors, including the type, age, weight, sex, and medical condition of the mammal, the severity of PAMIRS and its duration, and the particular anti-PAMIRS DSCG biologue being administered. An ordinarily skilled physician, dentist, or veterinarian, subsequent to the diagnosis of a PAMIRS, will readily determine and prescribe the effective amount of the anti-PAMIRS DSCG biologue to arrest the progress of the condition. In so proceeding, the physician, dentist, or veterinarian would, for example, employ relatively low dosages of the anti-PAMIRS DSCG biologue subsequently increasing dose until a maximum response was obtained. Such a response is obtained when the demineralization begins to decrease and subsequently substantially ceases, or at a minimum remains much reduced.

The anti-PAMIRS DSCG biologues are the various anti-allergenic agents known in the art as discussed above. Such substances include DSCG, other anti-allergenic bis chromones, anti-allergenic benzopyrans and anti-allergenic oxamic acids or derivatives (oxamates).

When DSCG is employed as the anti-PAMIRS DSCG biologue the compound is most preferably administered by insufflation at a dosage of 5-20 mg per patient per dose or equivalent parenteral dosages. This compound is not orally active for anti-PAMIRS purposes. When dosages significantly higher than 20 mg per patient by insufflation are employed, the systemic toxicity of DSCG must be carefully evaluated and subsequent dosages determined by evaluating the benefit of the drug in relation to any such toxic manifestations. For anti-PAMIRS bis chromones other than DSCG insufflation as a route of administration is preferably employed and an effective dosage equivalent to the DSCG dose above is determined and employed by methods known in the art. See U.S. Pat. No. 4,046,910 describing the methods by which relative potencies, and thus relative dosages, are determined for various anti-PAMIRS bis chromones.

Initial dosages of the anti-PAMIRS oxamate or benzopyran between 0.1 and 100 mg per patient per dose orally are employed. However, when dosages as high as about 100 mg per patient per dose orally are employed, the systemic toxicity of the anti-PAMIRS oxamate or benzopyran must be carefully evaluated and subsequent dosages determined by evaluating the benefit of the drug in relation to any such toxic manifestations. Effective dosages for anti-PAMIRS oxamates or benzopyrans are determined and employed by methods known in the art. See U.S. Pat. No. 4.046,910 describing the methods by which relative potencies, and thus relative dosages, are determined for such compounds employing standard animal tests (e.g., rat PCA described therein).

In order to obtain the efficacious result provided by the present invention, a route of administration permitting systemic action is required, as indicated above. Especially preferred are topical applications where localized effects are exerted upon absorption. Thus in the treatment of a PAMIRS secondary to periodontal disease, oral liquid (e.g., mouthwashes) or gels or viscous fluids (e.g., toothpastes and tooth gels) are preferred vehicles.

For anti-PAMIRS DSCG biologues known to be orally active, the oral route of administration is preferred.

Parenteral routes of administration provide the desired activity at the appropriate equivalent dose, as determined above. Thus, the present method provides intravenous injection or infusion, and subcutaneous injection. Regardless of the route of administration selected, the anti-PAMIRS DSCG biologue is formulated into pharmaceutically acceptable dosage form by conventional methods known to the pharmaceutical art.

When powders, pastes or gels are required, the anti-PAMIRS DSCG biologue is conveniently formulated by mixture into conventional dentifrices. In the case of parenteral administration, sterile solutions for injection or infusion are prepared in accordance with readily available techniques.

The various carboxyl-containing anti-PAMIRS agents are all employed in any conventional, pharmaceutically acceptable form. Thus these agents are optionally employed as free acids, esters, or salts.

The use of the anti-PAMIRS DSCG biologue is, by a further embodiment of the present invention, undertaken concomitantly with other forms of conventional therapy for a PAMIRS. Such other forms of conventional therapy include, for example, the various chemical therapies described in U.S. Pat. No. 4,125,621. When such combination therapies are employed, significant anti-PAMIRS effects are often obtained with reduced effective dosages of the anti-PAMIRS DSCG biologue agent employed herein.

In accordance with this further embodiment of the present invention, there are provided novel pharmaceutical compositions for anti-PAMIRS therapy. These novel compositions consist of combinations of two or more active agents, one such agent being in instant anti-PAMIRS DSCG biologue and the second and further agents being the heretofore known agents for the treatment for osteoporosis and osteoporotic conditions. Such previously known anti-osteoporotic agents include anabolic steroids, estrogenic steroids, calcium salts, inorganic fluoride, and calcitonin from various sources. Such novel compositions are advantageously used in arresting a PAMIRS, often permitting a reduced dosage of the instant anti-PAMIRS agent than that which would be required were it the sole therapy for arresting or preventing the PAMIRS.

In these novel pharmaceutical compositions, the instant anti-PAMIRS DSCG biologue is employed for each unit dosage in an amount equal to the amount of the instant anti-PAMIRS DSCG biologue were it the sole therapy down to an amount not less than 50% thereof. The other conventional anti-PAMIRS or agent or agents are present therein at the known amounts employed in the treatment of osteoporosis.

Moreover, the present invention further provides novel compositions of the instant anti-PAMIRS DSCG biologues exhibiting extraordinary convenience as a result of the topical activity of these agents in the treatment of dental PAMIRS. Employed in these novel dentifrice and mouthwash compositions are conventional ingredients except for the anti-PAMIRS DSCG biologue.

Such dentifrices contain an effective amount of the anti-PAMIRS DSCG biologue such that an application of a pre-determined quantity of the dentifrice to the teeth and gingiva results in the desired anti-PAMIRS effect. Such dentifrices are formulated by conventional means as is known in the art, and particularly include the combination of an instant anti-PAMIRS DSCG biologue with a conventional dentifrice (e.g., commerically available toothpastes, tooth gels, or tooth powders). Such dentifrices are particularly useful in the topical treatment of PAMIRS secondary to periodontal disease, as described above.

Similarly, the instant invention relates to the further oral composition comprising the anti-PAMIRS DSCG biologue in solutions adapted for mouthwashes. In accordance with such novel compositions, the instant anti-PAMIRS DSCG biologue is present in the conventional mouthwash solution at a concentration such that a pre-determined volume of the mouthwash contains an amount of the anti-PAMIRS DSCG biologue effective to exert the desired anti-PAMIRS effect on contact with the oral tissues.

Further, novel compositions containing known anti-inflammatory steroids are provided. These combinations represent preferred vehicles for treatment of diseases with anti-inflammatory steroids and employ an effective amount of an anti-PAMIRS DSCG biologue with standard amount of the steroid.

The foregoing novel compositions are preferably provided in unit dosage or package dosage forms, where the composition consists of an amount of each pharmacological agent required for a single dose or a pre-determined series of doses over some pre-determined interval of time. For combination therapies, such unit or package dosages, therefore, may consist of a single pharmaceutical entity, containing therewithin both agents or a paired or otherwise ordered series of such discrete entities containing these agents separately. Hence, within the ambit of the novel pharmaceutical compositions provided herein are those which would include packages containing a multiplicity of discrete pharmaceutical entities in an ordered way for the administration of these novel compositions over a pre-determined period of time. For example, by a preferred embodiment of the present invention such novel compositions would include discrete pharmaceutical entities containing lesser or greater amounts of the novel anti-PAMIRS DSCG biologue at the time therapy is initiated with gradually increasing or decreasing amounts of the instant anti-PAMIRS DSCG biologue in discrete pharmaceutical entities intended for administration subsequently as therapy progresses.

Finally for the anti-PAMIRS DSCG biologues indicated above as orally active, there are provided in accordance with the present invention feeds and feed premixes containing amounts of the instant anti-PAMIRS DSCG biologue which, when present in the animal's feed, is at a concentration effective to exert the desired anti-PAMIRS effect. Such feed and feed premixes are made in accordance with readily known and available techniques particularly useful in the treatment of animals where the PAMIRS compromise the animal's economic value. Examples of a PAMIR which compromises the economic value of an animal include periodontal disease in sheep and horses, milk fever in lactating cattle, and bone diseases in egg-laying fowl.

Thus the method provided by the present invention provides for the systemic administration to a mammal an amount of an anti-PAMIRS agent effective to arrest or prevent a PAMIRS. The anti-PAMIRS agent contemplated for use in the present invention are those compounds known in the prior art and described in the aforementioned U.S. patents.

Examples of preferred anti-PAMIRS bis chromones are generically represented by formula I, wherein $R_1$, $R_2$, $R_3$, $R_4$, $R_5$, and $R_6$ are hydrogen, halogen (chloro, bromo, or iodo), lower alkyl (preferably alkyl of one to 4 carbon atoms, inclusive), hydroxy, or lower alkoxy (preferably alkoxy of one to 4 carbon atoms, inclusive);

wherein X is straight or branched chain polymethylene of 3 to 7 carbon atoms, inclusive, $-CH_2-CH=CH-CH_2-$, $-CH_2-CH_2-O-CH_2-CH_2-$, $-CH_2-CO-CH_2-$, $-CH_2-(o-Ph)-CH_2$, wherein o—Ph is 1,2-phenylene, $-CH_2-C(CH_2OH)(CH_2Cl)-CH_2-$, $-CH_2-CH(OH)-CH_2-$, or $-CH_2-CH(OH)-CH_2-O-CH_2-CH(OH)-CH_2-$; and the salts, esters, and amides thereof.

Particularly preferred as anti-PAMIRS bis chromones in accordance with the present invention are DSCG and the various other salt and ester forms thereof, which compounds are incorporated here by reference from U.S. Pat. No. 3,419,578.

Preferred among the anti-PAMIRS oxamates are the oxanilic acid derivatives represented by formula II and the phenylene dioxamic derivatives represented by formula III, wherein one of $R_2$, $R_3$, $R_4$, $R_5$, and $R_6$ is hydrogen or cyano;

wherein a second and a third of $R_2$, $R_3$, $R_4$, $R_5$, and $R_6$ are selected from the group consisting of hydrogen, nitro, amino, halo (fluoro, chloro, bromo, or iodo), alkyl (preferably alkyl of one to 4 carbon atoms, inclusive), hydroxy, alkoxy (preferably alkoxy of one to 4 carbon atoms, inclusive), and trifluoromethyl, being the same or different; and wherein the remainder of $R_2$, $R_3$, $R_4$, $R_5$, and $R_6$ are hydrogen.

The present invention thus provides a surprising and unexpected method of use and unexpectedly convenient and efficacious compositions of matter for a class of pharmacological agents previously known to be useful for unrelated pharmaceutical and other purposes.

DESCRIPTION OF THE PREFERRED EMBODIMENTS

The advantageous effects of the anti-PAMIRS DSCG biologues in accordance with the present invention are demonstrated by the experimental results, reported hereinafter, which are illustrative (but not limiting) as to the operation of the novel methods described above.

EXAMPLE 1

The inhibition of bone resorption in vitro as measured by the blockage of PTH-stimulated $^{45}Ca$ release from fetal rat bone by lodoxamide, N,N'-(2-chloro-5-cyano-m-phenylene)dioxamic acid, (as its bis-tris(hydroxymethyl)amino methane salt).

Following the procedure of Horton, J. E., et al., Science 199:1342–1345 (1978), the anti-PAMIRS activity of lodoxamide was assessed. The following experiments were undertaken.

A. Tests, whose results appear in Table I, were undertaken with media being maintained with or without PTSH (2 μg/ml) stimulation (column I of Table I) and with or without the oxamate (250 μg/ml) present (column II of Table I). The amount of radioactive calcium release (the mean release in percent) for the first 48 hours (column IIIA of Table I) and for hours 49–120 (column IIIB of Table I) is then reported. The results of Table I indicate the oxamate induces a statistically significant reduction in radioactive calcium release over the period of time in which the oxamate is present and demonstrates the effective anti-PAMIRS activity of the compound.

B. A further experiment indicates the inhibition of radioactive calcium release by the oxamate in a dose-dependent manner. Column I of Table II describes the various concentrations (μg/ml) of the oxamate Table II describes control values of radioactive calcium release at 120 hours (mean percentage release); and column III describes radioactive calcium release with stimulation by PTH (2μg/ml) and oxamate. As indicated by the results reported in Table II, the oxamate occasions a dose-dependent decrease in radioactive calcium release.

TABLE I

| I Stimulant | II Duration oxamate present (hrs) | III Mean (in %) of $^{45}$Ca release | |
|---|---|---|---|
| | | A 0–48 hr | B 49–120 hr |
| None | 0–48 | 11.64 | 3.63 |
| PTH | | 29.04 | 41.49 |
| None | 49–120 | 8.95 | 1.99 |
| PTH | | 36.77 | 26.98 |
| None | None | 10.03 | 3.82 |
| PTH | | 37.93 | 37.64 |

TABLE II

| I Oxamate (μg/ml) | II $^{45}$Ca Release (Mean in %) | III |
|---|---|---|
| | Control (No oxamate or PTH) | With Oxamate and PTH |
| 250 | 7.11 | 42.64 |
| 100 | 8.62 | 40.86 |
| 50 | 8.50 | 53.87 |
| 10 | 9.89 | 64.31 |
| 1 | 9.05 | 74.51 |
| None | 8.71 | 77.44 |

FORMULAS

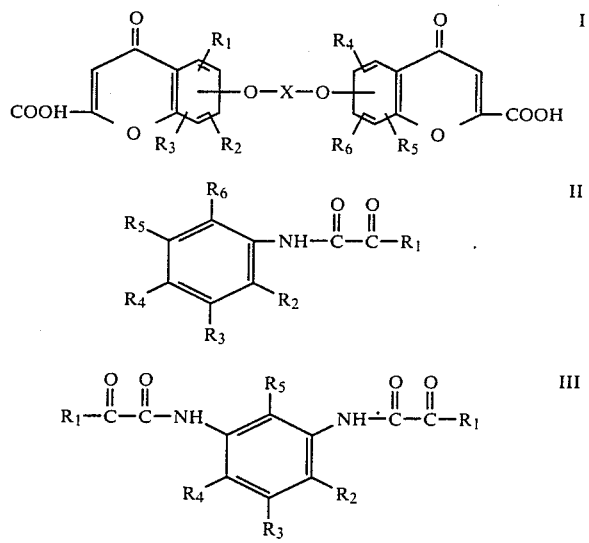

We claim:

1. A method of arresting or preventing bone resorption in an animal exhibiting or susceptible to development of bone resorption which comprises systemically administering to said animal an amount of DSCG effective to treat or prevent said bone resorption.

2. A method of arresting or preventing bone resorption in an animal exhibiting or susceptible to development of bone resorption which comprises systemically administering to said animal an amount of lodoxamide diethyl ester or lodoxamide bis-tham salt effective to treat or prevent said bone resorption.

* * * * *

UNITED STATES PATENT OFFICE
CERTIFICATE OF CORRECTION

Patent No. 4,501,754                       Dated      February 26, 1985

Inventor(s)    William J. Wechter and John E. Horton

It is certified that error appears in the above-identified patent and that said Letters Patent are hereby corrected as shown below:

Column 2, line 1, "memopause" should read -- menopause --.

Column 3, line 7, "4,202,688" should read -- 4,101,668 --.

Column 4, lines 24-25, "iodoxamide" should read -- lodoxamide --.

Column 4, line 25, "phenylene)amino methane salt" should read
-- phenylene)dioxamic acid as a bis THAM salt, tris(hydroxymethyl)-
amino methane salt --.

Column 4, line 32, "4,121,621" should read -- 4,125,621 --.

Column 4, line 33, "4,101,688" should read -- 4,101,668 --.

Column 5, line 30, "succeptible" should read -- susceptible --.

Column 7, line 36, "4.046,910" should read -- 4,046,910 --.

*Signed and Sealed this*

*Twenty-third* Day of *September 1986*

[SEAL]

Attest:

DONALD J. QUIGG

Attesting Officer                 Commissioner of Patents and Trademarks